（12） United States Patent
Gavaga (10) Patent No.: US 9,498,251 B2
(45) Date of Patent: Nov. 22, 2016

(54) EMBRYO TRANSFER (71) Applicant: Quinn A. Gavaga, Cache Creek (CA)

(72) Inventor: Quinn A. Gavaga, Cache Creek (CA)

( * ) Notice: Subject to any disclaimer, the term of this patent is extended or adjusted under 35 U.S.C. 154(b) by 176 days.

(21) Appl. No.: 14/059,001

(22) Filed: Oct. 21, 2013

(65) Prior Publication Data

US 2014/0179988 A1 Jun. 26, 2014

Related U.S. Application Data (63) Continuation-in-part of application No. PCT/CA2012/050407, filed on Jun. 19, 2012.

(60) Provisional application No. 61/499,351, filed on Jun. 21, 2011.

(51) Int. Cl.
*A61B 17/435* (2006.01)
*A61D 19/04* (2006.01)

(52) U.S. Cl.
CPC ............. *A61B 17/435* (2013.01); *A61D 19/04* (2013.01)

(58) Field of Classification Search
CPC ................... A61B 17/435; A61B 2017/4216; A61B 2217/005; A61B 2217/007; A61B 17/42; A61B 17/43; A61B 1/303
See application file for complete search history.

(56) References Cited

U.S. PATENT DOCUMENTS

| 4,632,110 A | 12/1986 | Sanagi |
| 4,653,475 A | 3/1987 | Seike et al. |
| 5,961,444 A | 10/1999 | Thompson |
| 2008/0119868 A1* | 5/2008 | Sharp ................ A61B 17/3421 606/119 |

* cited by examiner

*Primary Examiner* — Christine H Matthews
(74) *Attorney, Agent, or Firm* — Adrian D. Battison; Ade & Company Inc.

(57) ABSTRACT

An embryo from a female animal is transferred to another animal by determining presence of an embryo in the uterus of a donor animal by ultra-sonic imaging and inserting an endoscope vaginally into the uterus to a location adjacent the embryo. A tool of the endoscope projects to a position to extract the embryo washed into a container of the tool which is then closed by moving a closure part to enclose the embryo and extracting the endoscope to remove the embryo for transfer to a recipient animal. The fluid into the container can be controlled in pressure to maintain a required pressure generally matching that inside the uterus.

15 Claims, 7 Drawing Sheets

EMBRYO TRANSFER

This application is a continuation in part of Application PCT/CA2012/050407 filed Jun. 19, 2012 and claims the benefit under 35 USC 119 (e) of Provisional Application 61/499,351 filed Jun. 2, 2011.

This invention relates to an apparatus and method for embryo transfer from one female mammal to another. The description hereinafter primarily relates to mares where the commercial operation of transfer methods is desirable, but ineffective; but can relate to any female mammal.

BACKGROUND OF THE INVENTION

Embryo transfer (ET) is the process of harvesting an embryo or embryos from a donor and transferring it to a recipient. The process can be done surgically or non-surgically with the latter being the preferred method in bovine and equine species and the former being the preferred technique in smaller species such as porcine, ovine, caprine and canine.

Application for ET in the mare is commercially done for three main reasons; a donor mare in competition can produce and transfer an embryo and still compete while a recipient mare carries her genetics to a term pregnancy, to produce multiple pregnancies in one year, to transfer to a recipient mare when the donor mare is considered a high risk for pregnancy complications.

In cattle superovulation is a successful procedure where with hormone therapy multiple (average 6 but numbers as high as 40 reported) embryos can be harvested (flushed) in any one procedure. Unfortunately mares do not respond successfully to superovulation so a single procedure yields at best only one embryo. The exception is when a mare naturally double ovulates and thus two potential embryos might be retrieved. The average success of achieving a pregnancy through embryo transfer in the mare is 25%. The average cost per attempt is from $7000 to $12000 and the industry reports embryo transfer in mares to be approximately $250 000 000 annually worldwide. This means that $187 500 000 is spent with no results. This poor success has hindered the process of embryo transfer in mares from becoming a more main stream procedure.

The traditional method for transferring an embryo in mares is to aseptically pass a catheter through the vulva, vagina and cervix and into the uterine body. A cuff is inflated to seal the cervical uterine junction. The uterus is flushed with approximately 4 liters of specialized solution. The solution is filtered through a 20 micron filter. The filter is emptied into petri dishes and then the dishes are searched with microscopy to find an embryo. If found the embryo is isolated and washed in another specialized solution and then loaded into a transfer pipette. The recipient mare is aseptically prepared for transfer and the transfer pipette is passed through the vulva, vagina and cervix and into the uterine body where the embryo is deposited.

Special concern for timing is required for a successful pregnancy from an ET procedure. The procedure is considered to start at day 0 which is when the mare is observed to have ovulated. The sperm must be present in the fallopian tubes prior to ovulation. Fertilization takes place in the fallopian tubes shortly after ovulation and the embryo remains there for 5 days after which time it moves into the uterus. Flushing or retrieving the embryo is normally done at day 7 which allows for adequate time for the embryo to reach the uterus for it cannot be retrieved from the fallopian tube. After day 8 the embryo hatches from its protective shell called the zona pellucita which then makes the embryo more fragile to handle. So 7 days post ovulation achieves the highest success rates thus far. A uterus is dynamic and changes through the female cycle. For this reason a recipient mare must be synchronized with the donor mare and her uterus must be close to 7 days post ovulation which adds another level of difficulty to the procedure. At the time a flush is performed it is unknown whether there is a viable embryo present or not.

Attempts have been made to transfer embryos at later stages of development such as 11 to 14 days post ovulation. At 11 days post ovulation the embryo is visible to a highly trained practitioner using ultra-sonography. This would seem to be ideal as retrieval would only be attempted if there was a pregnancy visualized. Unfortunately no success has been achieved at this stage. It is hypothesised that the embryos were too fragile and didn't survive the procedure.

SUMMARY OF THE INVENTION

It is one object of the invention to provide an improved method and/or apparatus for use in embryo transfer.

According to one aspect of the invention there is provided a method for transfer of an embryo from a female animal comprising:

determining presence of an embryo in the uterus of a donor animal by ultra-sonic imaging;

inserting an endoscope vaginally into the uterus to a location adjacent the embryo;

operating a tool of the endoscope to extract the embryo into a container of the tool;

closing the container of the tool to enclose the embryo and extracting the endoscope to remove the embryo for transfer to a recipient animal.

Preferably the container includes two parts which move to a fully closed position.

This is preferably done by providing two hemi-spherical parts which rotate, or one of which rotates relative to the other from a first open position with one cupped inside the other to a closed spherical position sealing around the edges of the two parts. Other closure systems can be used for example a sliding sleeve arrangement around an inner tube which has a hole to collect the embryo.

Optionally there is provided a fluid supply duct for supplying fluid to the tool where the fluid supply duct opens into the closed container. In this case, there can be provided a pressure sensor for controlling pressure of the fluid inside the container to match that in the uterus. Pressure control may or may not be necessary within the closed scoop.

Preferably the container has a transverse dimension of at least 1.0 cm and preferably of the order of 1.5 cm.

Preferably the presence of the embryo is detected at a time period of the order of 11 days after insemination.

Preferably the endoscope is guided to a position within the uterus by passing through a separate guide tube inserted into the uterus through the vagina.

Preferably the guide tube is held against bending during operation of the tool so as to locate an end of the guide tube at a fixed position within the uterus. That is the guide tube is either rigid so that it cannot bend at all, or is semi-rigid so that it is adjustable in shape by bending at one or more points along its length but that it maintains that shape when in use, that is as it is inserted into the uterus through the vulva, vagina and cervix and during insertion and operation of the endoscope and tool.

It will be appreciated that the guide tube is typically inserted and guided manually by the veterinarian in many cases by feeling the position of the guide tube within the vagina of the animal by a hand inserted through the rectum. That is the end of the guide tube can be carefully guided and moved to its position within the uterus by the veterinarian feeling exactly where that end is in relation to the cervix.

The shape and arrangement of the guide tube is arranged so that the guide tube is held fixed relative to the uterus during operation of the tool so as to locate an end of the guide tube at a fixed position within the uterus. This provides a fixed point or basis for the functioning of the operating components of the endoscope for moving an end of the endoscope relative to an end of the guide tube with the end of the guide tube held in fixed position relative to the uterus. In this way the skilled veterinarian can operate the conventional operating components of bend, orientation and displacement of the end of the endoscope to accurately locate the end of the endoscope at a required position relative to the wall of the uterus.

Preferably the guide tube is held fixed relative to the uterus by locating the guide tube at the cervix.

Preferably the guide tube is located at the cervix by first and second inflating balloons with one inside the uterus at the cervix and the other outside the cervix in the vagina.

According to a second aspect of the invention there is provided a method for transfer of an embryo from a female animal comprising:

inserting an endoscope vaginally into the uterus to a location adjacent the embryo;

operating a tool of the endoscope to extract the embryo into a container of the tool;

guiding the endoscope to a position within the uterus by a guide tube inserted into the uterus through the vagina;

holding the guide tube fixed relative to the uterus during operation of the tool so as to locate an end of the guide tube at a fixed position within the uterus;

and operating components the endoscope for moving an end of the endoscope relative to an end of the guide tube.

Preferably the guide tube is held against bending during operation of the tool so as to locate an end of the guide tube at a fixed position within the uterus.

Preferably the guide tube is held fixed relative to the uterus by locating the guide tube at the cervix.

Preferably the guide tube is located at the cervix by first and second inflating balloons with one inside the uterus at the cervix and the other outside the cervix in the vagina.

Preferably the endoscope and the tool are inserted into the guide tube when the guide tube is in fixed position with the end of the guide tube within the uterus.

Based on the augmentation and refinement to the method of embryo described herein, retrieval at 9 to 13 days and more preferably 11 or 12 days can achieve success rates in excess of 80%.

In the equine uterus a cascade of events begins in which, if no embryo is present, the uterus undergoes changes and the reproductive system starts the process toward ovulation. If a viable embryo is present in the uterus it blocks the hormone and chemical pathways that initiate the cascade to ovulation thus pregnancy is maintained. At the time of transfer on day 11 or 12 the recipient's reproductive track is already undergoing changes that may make it unable to maintain a pregnancy.

In the present method, the recipient and the donor both are bred at the same time and an embryo is removed from the recipient mare and exchanged for an embryo from the donor mare. The delicate nature of the embryo is a very important consideration for success of this procedure so highly specialized equipment has been designed to overcome this.

Using this modified embryo transfer technique the procedure is cost effective and is a more attractive method of breeding in the equine industry.

BRIEF DESCRIPTION OF THE DRAWINGS

One embodiment of the invention will now be described in conjunction with the accompanying drawings in which:

FIG. 7 is a vertical cross sectional view through a tube for locating within the uterus of the animal the endoscope and tool of FIG. 1 for extraction of an embryo.

In the drawings like characters of reference indicate corresponding parts in the different figures.

DETAILED DESCRIPTION

Endoscopes are a well known device widely used in surgery and other procedures and comprise a tube with a camera and illumination which can be passed through an opening into the interior of the body and which can be manipulated to different positions. A central bore allows a tool to be passed through the tube for acting on the interior, many different tools are available. Typically a collar is provided which can be inflated to locate the tube at a required portion and to seal the opening relative to the tube. Arrangements of this type are widely used and well known to persons skilled in the art so that further details are not required.

Figure 1:
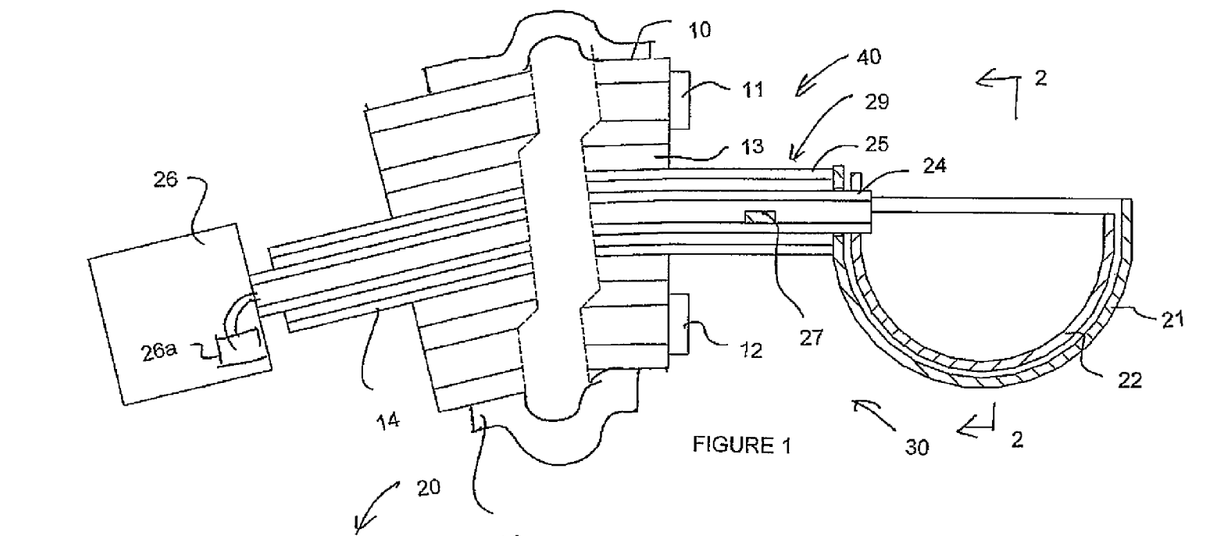
FIG. 1 is a vertical cross sectional view through a tool for use in an endoscope for extraction of an embryo, showing the tool in an initial open position.

FIG. 1 shows a recovery tool for use as part of a modified endoscope 40 including a tube 10 with a camera lens 11 and an illumination source 12 carried on the tube and including fiber optic communication from a distal end 10A of the tube 10 to control systems of the endoscope and the near end for operation by the user. The tube 10 is arranged so that it can be passed through an opening, in this case the vagina into the interior of the body. The tube includes components (not shown) which allow the end 10A to be manipulated to different positions. One or more central bores 13 or ports allow a tool 14 to be passed through the tube. Typically a collar 15 is provided which can be inflated to locate the tube at a required portion and to seal the opening, in this case the uterus, relative to the tube.

Through one of the working ports 13 of the endoscope is inserted a grasping tool 30. The grasping tool is small globe 20, approximately 1.5 cm in diameter. The globe has two hemispherical halves 21 and 22 one of which rotates by sliding slides inside the other. The components are made out of surgical grade stainless steel.

Figure 2:
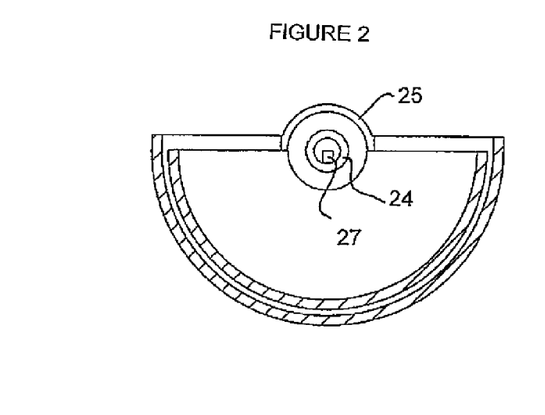
FIG. 2 is a cross-sectional view along the lines 2-2 of FIG. 1.
Figure 2A:
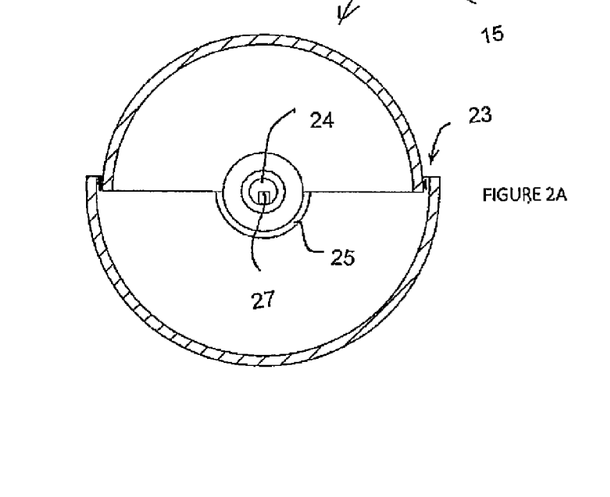
FIG. 2A is a cross-sectional view along the lines 2-2 of FIG. 1 showing the tool in the closed position after collection of an embryo.
Figure 3:
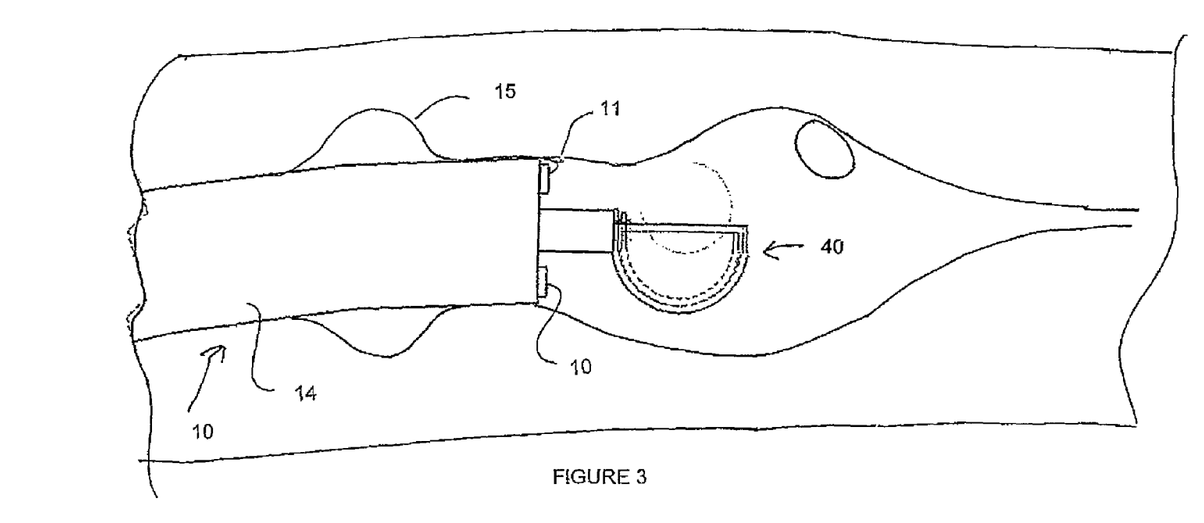
FIGS. 3 and 4 show the operation of the tool in a method of extraction.

When closed as shown in FIG. 2 the two parts 21 and 22 form a sealed unit or globe 20 with a sealing edge 23. The inner part 22 is rotated around the axis of the sphere by an operating element 24 at the end of the tube 10 which is operated by a control at the near end of the tube from the open position where the inner part is wholly within the outer part to form a hemi-spherical scoop to a closed position in which the globe is closed and sealed. This globe also has a fluid port 25 within it so fluid can be added or withdrawn from the globe 20. The fluid supply system 26A of a control unit 26 for supply to the port 25 passes through the tube 14 and includes an inline pressure sensor 27 sensitive to the internal pressure in the line and therefore within the closed globe 20. The supply 26A of the control unit 26 can be operated so that holding fluid can be supplied or removed to adjust the internal pressure in the globe 20 to match the same pressure as that of a normal uterine environment for that stage of embryo. The pressure within the uterus can be measured in situ or can be predetermined from historical measurements.

The special tool described above can in some embodiments be used with a stock endoscope. The tool can alternatively be a permanent "biopsy tool" which is manufactured by assembly into place in an endoscope from a typical supplier, but where the tool is not be able to be removed after it is manufactured into the scope. This is due to the fact that the typical globe is too large for the portal through the tube of a typical endoscope.

The tool operates in a similar manner to an ice cream scoop. In the open position one half of the globe 20 is rotated inside the other half as shown in FIG. 2A. The neck 29 of the tool that passes through the endoscope portal 13 is formed from two flexible tubes 25 and 24 one inside the other. The outer tube 25 is fixed to the bottom half 21 of the globe and the inner tube 24 is fixed to the top half of the globe. At the operator end the user operates the device 26 by activating a turning movement to the inner tube 24 so that it rotates the top half of the globe to close it. The inner tube 24 also provides the fluid port which is optional.

Figure 4:
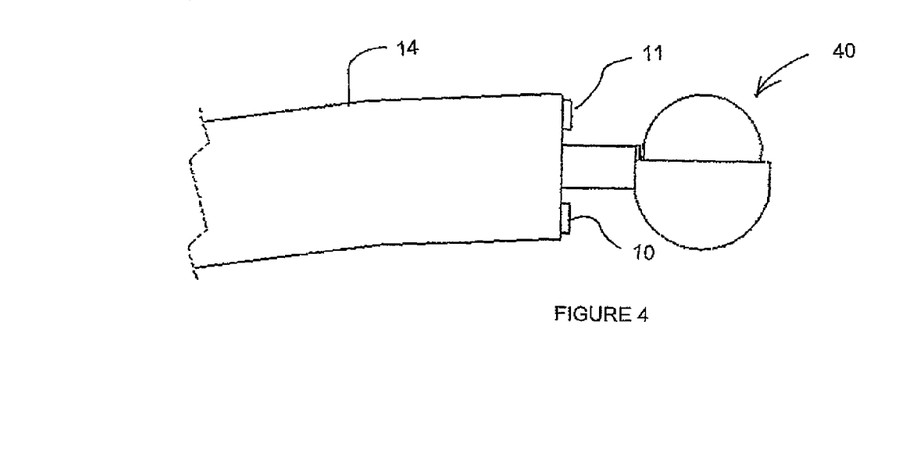

When the tool is first inserted as shown in FIG. 4 in the open position and the collar 15 inflated to hold the tool in place, once the tool is passed into visual proximity of the embryo it can be used to pick up the embryo.

Endoscopes have the ability to pass fluid through the port 13 or through a separate special port (not shown) to dilate the inside of the tube 14 or open the lumen of the uterus.

Thus most endoscopes have a small port adjacent to the lens. This port typically has a very small metal deflector that directs water across the lens to clean it should it become obscured with mucus or other debris. The air required in the present method can also be passed through this port. There is a pump on the power unit that works the scope. At the operator end there is a two stage valve that is normally worked by the index finger. With light depression air is pumped through the port adjacent to the lens that is normally used for insufflation to allow for dilation which enhances passage of an endoscope. If the valve is fully depressed fluid is pumped through to clean the lens.

This fluid supply through the endoscope is used to open the uterus and to infuse a small amount of fluid into the uterus to float the embryo away from the tissue of the uterus wall so that it can be simply picked up with the scoop. Air or air and fluid may be used to insufflate the uterus to allow for better visualization and pull the majority of the endometrium away from the embryo. Fluid may then be used to completely free the embryo or the tool can be used to pick up the embryo at that point, if its positioning is good and endometrial contact is minimal.

Once the embryo is in view the cuff 15 will be inflated so that if further fluid is infused the embryo will not float away. When insufflation is normally done there is constant loss of air along the outside of the scope but once the embryo is in view, the cuff 15 is inflated so constant insufflation is no longer needed and dilation of the uterus can be static.

It is necessary to control the supply and volume of fluid to prevent the embryo from floating too far away. In normal instances, because the pressure in the inflation collar 15 is kept low, the natural closure/collapse of the tissue of the uterus around the collar and the tool keeps a partial seal around the instrument and provides a slope running away from the collar 15 to prevent the embryo from falling into the area of the collar 15 where it become impossible to retrieve. The injection of fluid through the endoscope typically is required because of the fragile and movable nature of the embryo. In FIG. 4, the inflation collar 15 is close to the end of the endoscope at the location of the tool since this better locates the tube 14 and allows better control over movement of the tool. The third fluid supply tube 25 is optional but when provided acts to bathe the embryo.

When the embryo has been picked up, the tool is retracted from the donor animal and moved to the recipient. Once the embryo is placed in the recipient and the globe re-opened to release the embryo, fluid can be infused into the bottom of the globe and the embryo floated out.

The complete procedure is as follows:

1. The donor mare is synchronized in her estrous cycle with recipient mare sufficiently that they are in synchronism; or the recipient can be as much as 24 hours ahead or 72 hours but preferably not more than 48 hours behind the donor mare in her ovulation.

2. Both mares are bred on their synchronized ovulation as per normal breeding methods.

3. At earliest possible time post ovulation an embryo is searched for via ultrasonography in both the donor and recipient mares. Currently this is carried out at day 11 post ovulation when the embryo is sufficiently large to be determined by this method.

4. Once pregnancy is confirmed by the ultra-sound image in both the donor and recipient the embryo transfer and exchanged is commenced.

5. The donor and recipient mares are prepared pre-embryo recovery for a normal aseptic embryo recovery technique. Ideally the recipient mare is pregnant but that is not absolutely necessary. This transfer can still be attempted if the recipient is not pregnant but still in synchrony with the donor.

6. The procedure starts with the recipient where the recipient is sedated for ease of recovery and transfer.

7. In the recipient, a first technician operates the ultrasound imaging system to locate and document where the embryo is residing.

8. A second technician passes the recovery scope vaginally using normal aseptic palmed delivery to the cervix and the cervix is digitally enlarged and the scope is then advanced through the cervix and the operators hand is removed. The scope is then advanced until it appears on the ultrasound adjacent to the embryo. The ultrasonographer may or may not stop at this time. One the embryo is found via ultrasound the ultrasound is removed and the perineum washed thoroughly and the scope is passed into position.

9. Once the scope is in view with the embryo, the uterine horn is insufflated by air or air and fluid supply enough to free the majority of endometrial contact with the embryo. The uterus is infused with the fluid through the supply tube 25 with a fluid, such as a commercially available embryo recovery medium, to float the embryo. The inflation cuff 15 on the end of the recovery scope is arranged to prevent washing the embryo away. The embryo is captured with the grasping tool 20 on the recovery scope. The grasping tool 20 on the working end 10A of the recovery scope 10 is now a closed and is infused with the commercially available embryo holding fluid. The recovery scope is withdrawn from the uterus. From the recipient animal, the embryo is discarded or kept for other purposes.

10. The step 9 is repeated with the donor mare.

11. The recovery scope is washed with warmed alcohol and then 1 liter of warmed saline 12. The recipient mare is sedated again if necessary and her perineum washed again.

13. The recovery scope, now containing the donor's embryo is passed using normal aseptic palmed delivery to the cervix and the cervix is digitally enlarged 14. The recovery scope is then advanced to the location from where recipients own embryo was removed. The embryo is deposited in the uterus at the bifurcation of the uterine horns. The grasping tool 20 is opened and the embryo is either dumped by turning the whole tool by the base tube 29 to invert the cup or expelled with fluid. The recovery scope is withdrawn and the procedure is complete.

The mare is checked via ultra sound immediately after the procedure for embryo placement. The mare is checked by ultrasound imaging at 6 and 24 and 48 hours post-transplant for embryo viability and procedure success.

Figure 5:
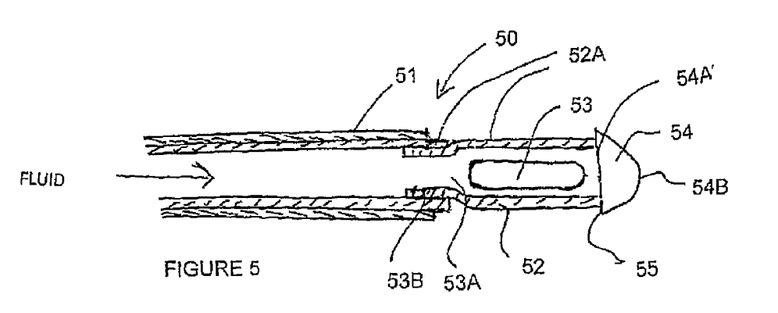
FIG. 5 is a vertical cross sectional view through a second embodiment of tool for use in an endoscope for extraction of an embryo, showing the tool in an initial open position for insertion through the tube of the endoscope.
Figure 6:
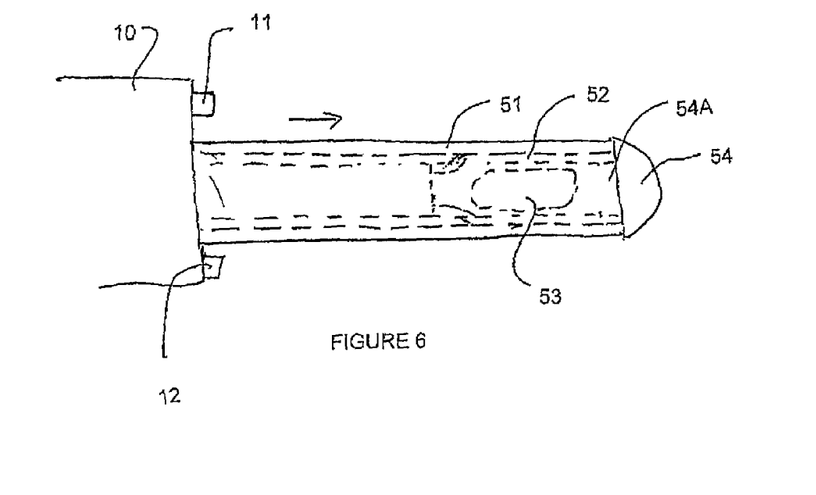
FIG. 6 is a top plan view through of the tool of FIG. 5 in the closed position after insertion through the tube of the endoscope and collection of the embryo.

Turning now to FIGS. 5 and 6, a second embodiment of the tool 50 is shown which is formed of an outer sleeve 51 slideable on the outer surface of a tube 52 inside the sleeve 51. The tube 52 has an end portion 52A projecting beyond an end of the sleeve 51 which connects to a cylindrical stainless steel tip member 54. The tip member is typically 2 to 3 cms long and has an elongate slot 53 in one side leading to a hollow interior 53A. The tip member includes a portion 53B which is necked down to a reduced diameter onto which the end portion 52A of the tube 52 is engaged. The hollow interior 53A of the tip member 54 communicates with the interior of the tube 52 allowing access to the interior of the tube 52. The tube 52 and the sleeve 51 are both formed of a medical grade plastics material allowing some flexibility. The stainless steel tip member 54 has an end closure portion 54A which closes the front end of the tip member. The metal tip member thus has a hole in the hollow interior that communicates with the slot 53 so that fluid can be passed from the inner tube 52 into the slot 53. The outer face 54B of the closure portion 54A is domed or hemi-spherical to provide a smooth rounded surface of a transverse diameter or the order of 1.0 cms. The diameter of the tip member is lightly larger than that of the outer surface of the cylindrical portion of the tip member 54 to provide a shoulder 55 surrounding the end of the tube to provide an abutment for the end of the sleeve. In operation the endoscope is maneuvered to the required position and the tool 50 inserted through the bore 13 to the location of the embryo. As described previously, fluid can be supplied through the tube 52 through the opening 53 to the uterus to wash out the embryo from its position. When exposed, the embryo is scooped by rotating the tool so that the opening 53 is moved to the embryo to allow it to enter into the interior of the metal tip within the slot and not enter the tube. When the embryo is captured, the sleeve is moved longitudinally to close the hole by covering the tip portion 52A up to the tip member 54 allowing the tool and captured embryo to be extracted. The fluid control systems previously described are used to ensure the protection of the captured embryo.

Turning now to FIGS. 7 to 10, there is shown the tool 14 inserted through the endoscope 40 which is guided to a position within the uterus 62 by a guide tube 50 inserted into the uterus 62 through the vulva 60, the vagina 61 and the cervix 63.

The guide tube is rigid during insertion and during operation of the endoscope 40 and tool 14 so as to locate an end 51 of the guide tube 50 at a fixed position within the uterus 62. Guiding to the required position is controlled by the veterinarian by holding the proximal end 52 and by feeling the location of the distal end 51 relative to the cervix through the bowel wall.

Figure 8:
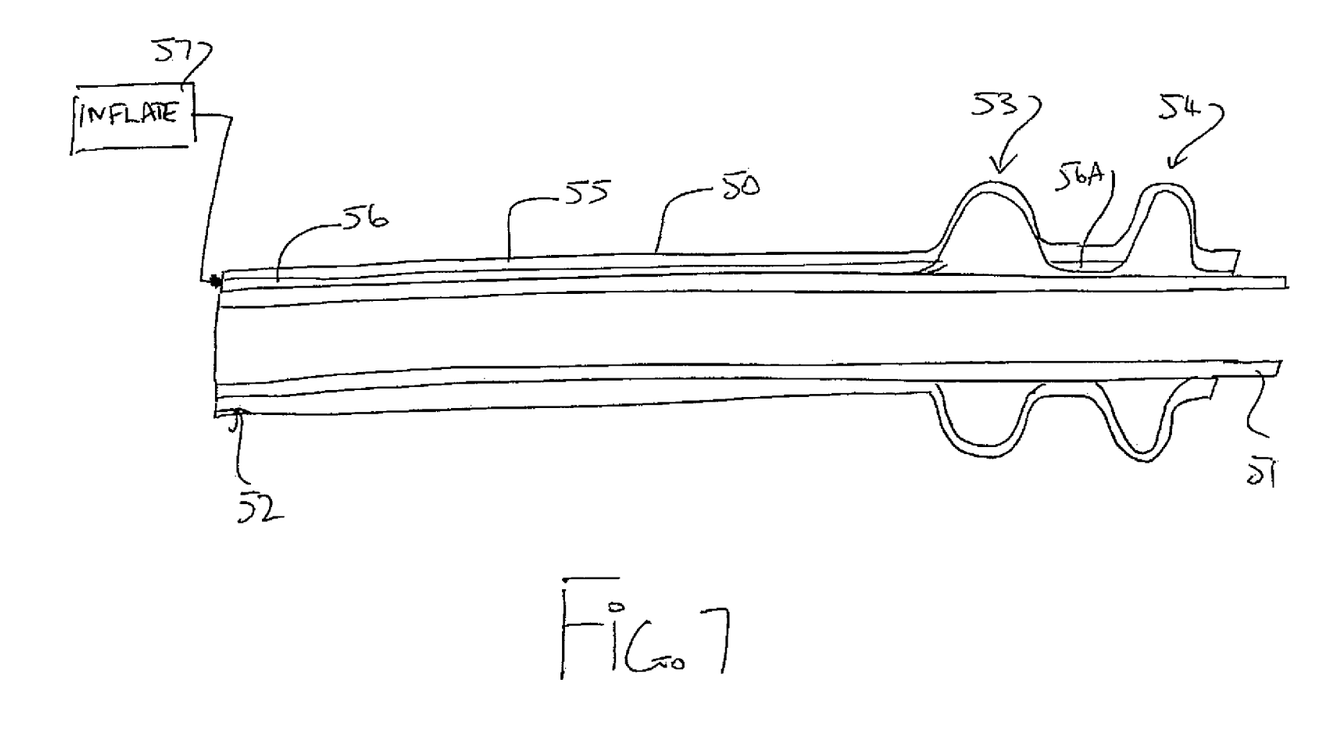
FIG. 8 is a vertical cross sectional view on an enlarged scale through the remote end of the tube of FIG. 1 showing the insertion and operation of the endoscope.
Figure 10:
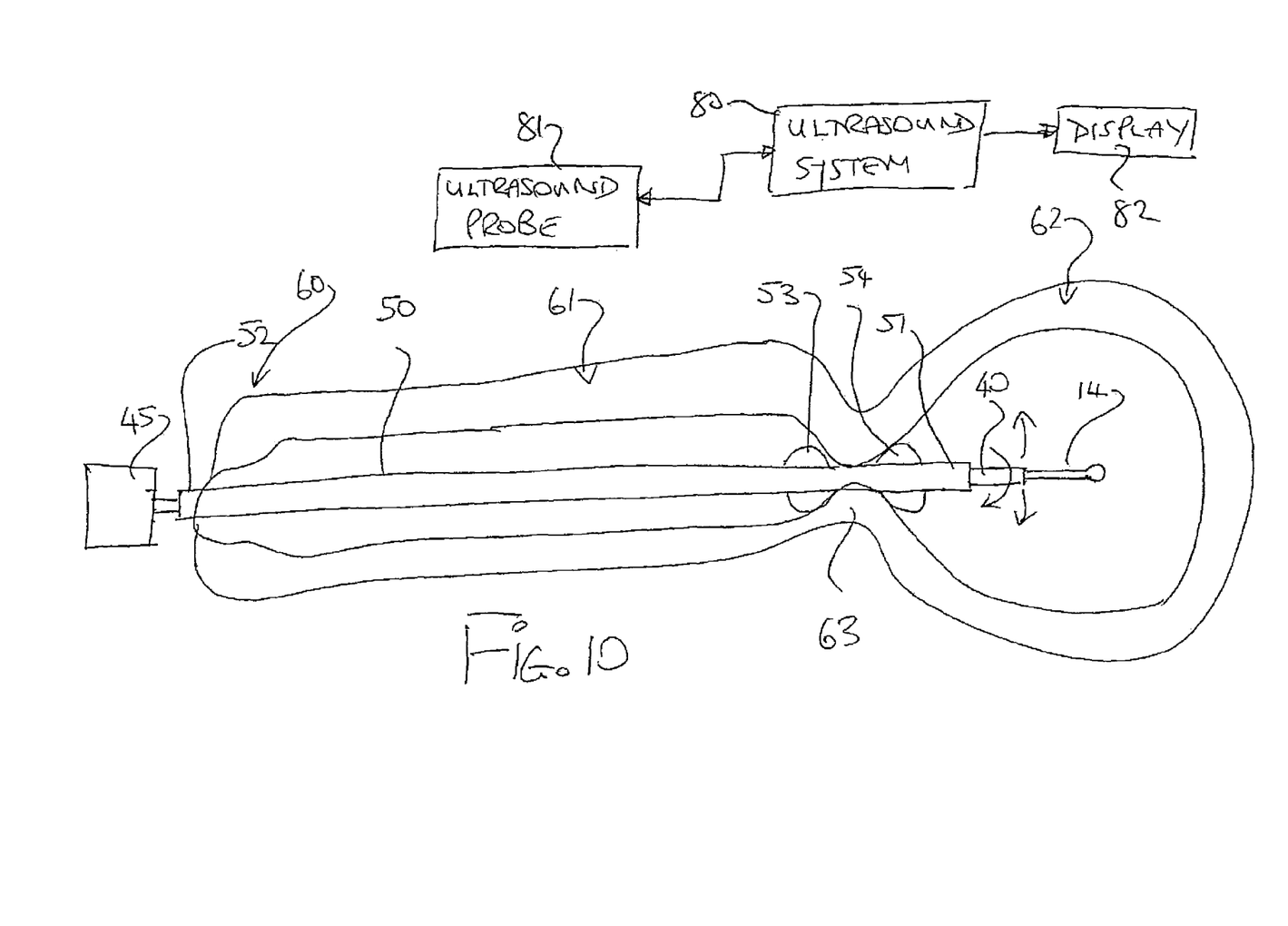
FIG. 10 is a vertical cross sectional view on a reduced scale the tube of FIG. 1 together with the endoscope and the tool of FIG. 1 showing the components in position inserted through the vulva, vagina and cervix of the animal into the uterus.

After insertion, the guide tube 50 is held fixed relative to the uterus during operation of the tool so as to locate an end of the guide tube at a fixed position within the uterus by locating the guide tube at the cervix. The guide tube is located at the cervix by first and second inflating balloons 53, 54 on an exterior surface of the tube 50 with one 54 inside the uterus at the cervix and the other 53 outside the cervix in the vagina. Thus the cervix is located between the two balloons to prevent longitudinal movement of the tube when the balloons are inflated. Also the cervix is relatively stiff and positioned at a fixed location relative to the interior wall of the uterus so that the tube is held at a fixed location to allow the veterinarian to operate the endoscope to locate its end at a required position adjacent the wall of the uterus.

The endoscope 40 includes operating components for moving an end of the endoscope relative to an end of the guide tube with the end of the guide tube held in fixed position relative to the uterus.

The balloons 53, 54 are defined on an outside of the body of the tube 50 by a layer of a resilient material 55 covering the body of the tube 50 which is cast in place or applied to define a passage 56 from the end 52 to the first of the balloons which then communicates with a passage 56A to the end balloon. The balloons are formed by thinner annular sections of the covering 55 so that the annular sections inflate preferentially relative to the remainder of the covering to form annular balloons surrounding the tube body and extending over a limited extent longitudinally of the tube. The spacing between the balloons is designed to match approximately the thickness of the cervix to hold the cervix between them. In this way the balloons are inflated by an inflation pump 57 when the veterinarian has determined that the tube is at the required location to hold the tube at fixed position longitudinally and radially.

The balloons can be inflated independently by separate passages if required which can be used to locate the tube more effectively by locating it from one side of the cervix before the second balloon is inflated.

The endoscope is then inserted into the guide tube when the guide tube is in fixed position with the end of the guide tube within the uterus.

Figure 9:
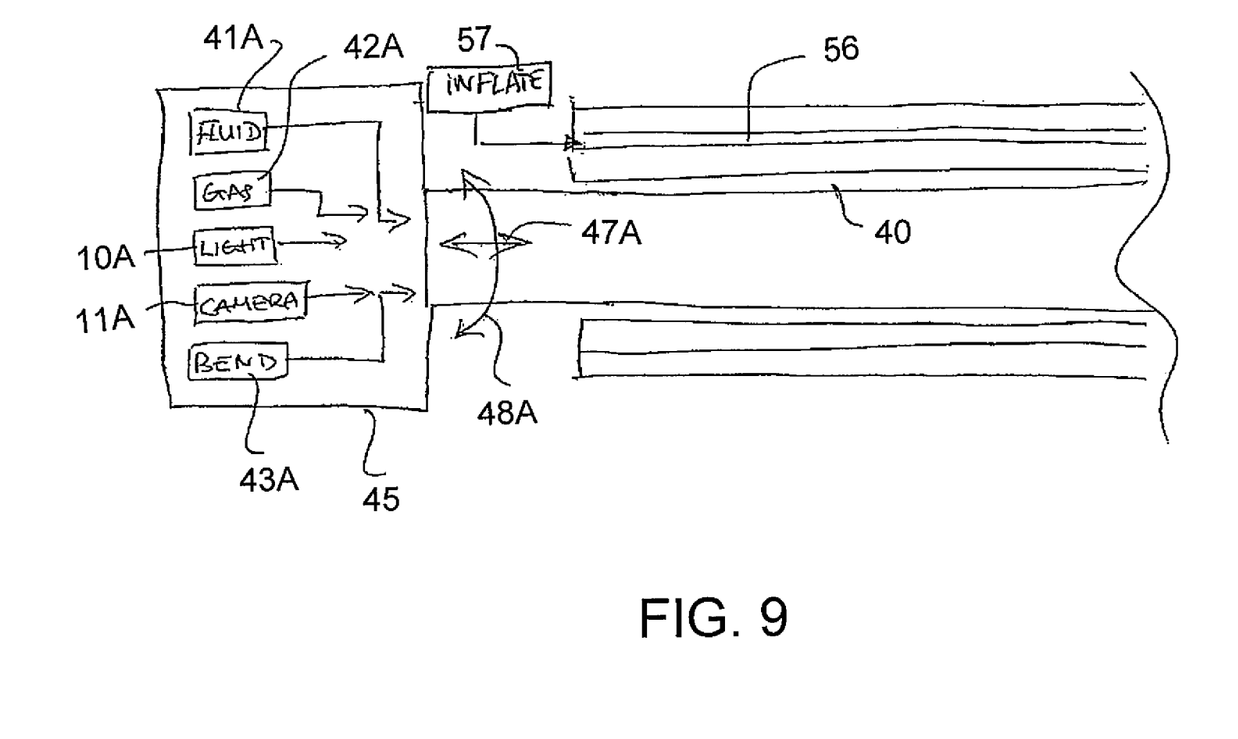
FIG. 9 is a vertical cross sectional view on an enlarged scale through the proximal end of the tube of FIG. 1 showing the control system of the endoscope.

The endoscope 40 includes a conventional control system 45 operable by the veterinarian including operating components of the endoscope. These include a fluid supply 41A for supply of a fluid to the end of the endoscope at a nozzle 41;

a gas supply 42A for supply of a gas to the end of the endoscope at a nozzle 42; a camera control 11A for operating the camera 11 and a light control 10A for operating eh illumination 10. The endoscope also includes a manually operable control 43A for operating bending elements (not shown) for bending the end of the endoscope to sides of an axis of the tube 50. Typically this is effected by a wire pulling system which pulls on the end differentially to effect bending to one side. In addition the control system can be manually moved longitudinally as indicated at 47A to push the end in and out of the tube 50 longitudinally as indicated at 47. Also the control system can be manually rotated angularly around the axis of the tube 50 as indicated at 48A to rotate the end as indicated at 48. These controls thus allow movement of the end of the endoscope to required positions within the uterus relative to the fixed or stable end of the guide tube which is held in fixed position relative to the uterus. The tool 14 can be inserted after the required adjustment movement or can be in place while that movement is being effected.

The ultrasound system for guiding the extraction of the embryo by the veterinarian is schematically illustrated in FIG. 10 at 80 and includes a probe 81 and a display 82. This enables the veterinarian to view the position of the embryo and to use the tool to extract the embryo as previously described.

The invention claimed is:

1. A method for raising a mammalian animal comprising:
   transferring an embryo from a uterus of a female donor mammalian animal in pregnancy to a uterus of a female recipient mammalian animal;
   and raising the embryo to full term in the recipient animal;
   wherein the embryo is transferred by steps comprising:
      providing an ultrasonic imaging system and an endoscope having a camera;
      waiting in the pregnancy of the donor animal until the embryo is observable in an ultrasonic image taken by the ultrasonic imaging system of the uterus of the donor animal and is visible in an image generated by the camera of the endoscope of the uterus of the donor animal;
      determining a presence and location of the embryo on a wall of the uterus of the donor animal from said ultrasonic image;
      inserting a remote end of the endoscope vaginally into the uterus of the donor animal to a location adjacent the embryo;
      the remote end of the endoscope carrying a scoop member;
      operating the scoop member to cause the embryo to enter the scoop member from the wall of the uterus;
      the remote end of the endoscope carrying an enclosing member for covering the scoop member to enclose the embryo;
      operating the enclosing member to enclose the embryo within the scoop member after the embryo has been scooped up into the scoop member;
      extracting the endoscope to remove the embryo in the scoop member from the uterus of the donor animal;
      and transferring the embryo to the uterus of the recipient animal.

2. The method according to claim 1 wherein operating the scoop member includes rotation to scoop up the embryo from the wall of the uterus.

3. The method according to claim 1 wherein the scoop member and the enclosing member are moved to a fully closed position.

4. The method according to claim 1 wherein the scoop member and the enclosing member comprise two hemispherical parts which are rotated from a first open position with one inside the other to a closed spherical position.

5. The method according to claim 1 including supplying fluid to the scoop member through a fluid supply duct.

6. The method according to claim 1 wherein the scoop member has a transverse dimension of at least 1.0 cm.

7. The method according to claim 1 wherein presence of the embryo is detected at a time period in the range of 9-13 days after insemination.

8. The method according to claim 1 including providing a guide tube though which the endoscope passes, inserting the guide tube into the uterus through the vagina, holding the guide tube fixed relative to the uterus at the cervix of the uterus so as to locate an end of the guide tube at a fixed position within the uterus, inserting the remote end of the endoscope though the guide tube, and, while holding the end of the guide tube fixed, operating the endoscope to move the remote end relative to the end of the guide tube to move the remote end to a position within the uterus adjacent the embryo on the wall.

9. The method according to claim 8 wherein the guide tube is held fixed relative to the uterus by locating the guide tube at the cervix.

10. The method according to claim 9 wherein the guide tube is located at the cervix by first and second inflating balloons with one of the balloons inside the uterus at the cervix and the other balloon outside the cervix in the vagina.

11. A method for raising a mammalian animal comprising:
    transferring an embryo from a uterus of a female donor mammalian animal in pregnancy to a uterus of a female recipient mammalian animal;
    and raising the embryo to full term in the recipient animal;
    wherein the embryo is transferred by steps comprising:
       providing an endoscope having a camera;
       determining a presence and location of the embryo on a wall of the uterus of the donor animal;
       inserting a remote end of the endoscope vaginally into the uterus of the donor animal to a location adjacent the embryo on the wall of the uterus of the donor animal;
       operating the endoscope to move the remote end to a position within the uterus adjacent the embryo on the wall;
       the remote end of the endoscope including an elongate carrying member projecting outwardly from the remote end so as to extend toward the wall;
       the elongate carrying member carrying a scoop member forming a bowl;
       the elongate carrying member being movable in rotation around an axis longitudinally of the elongate carrying member;
       operating the scoop member including rotation to scoop up the embryo from the wall of the uterus;
       providing an enclosing member for covering the scoop member to enclose the embryo;
       operating the enclosing member to enclose the embryo within the scoop member after the embryo is scooped up;
       extracting the endoscope to remove the embryo in the scoop member from the uterus of the donor animal;
       and transferring the embryo to the uterus of the recipient animal.

12. The method according to claim 11 including providing a guide tube though which the endoscope passes, inserting the guide tube into the uterus through the vagina, holding the guide tube fixed relative to the uterus at the cervix of the uterus so as to locate an end of the guide tube at a fixed position within the uterus, inserting the remote end of the endoscope though the guide tube, and, while holding the end of the guide tube fixed, operating the endoscope to move the remote end relative to the end of the guide tube to move the remote end to a position within the uterus adjacent the embryo on the wall.

13. The method according to claim 12 wherein the guide tube is held fixed relative to the uterus by locating the guide tube at the cervix.

14. The method according to claim 13 wherein the guide tube is located at the cervix by first and second inflating balloons with one of the balloons inside the uterus at the cervix and the other balloon outside the cervix in the vagina.

15. A method for raising a mammalian animal comprising:
    transferring an embryo from a uterus of a female donor mammalian animal in pregnancy to a uterus of a female recipient mammalian animal;
    and raising the embryo to full term in the recipient animal;
    wherein the embryo is transferred by steps comprising:
        providing an endoscope having a camera;
        determining a presence and location of the embryo on a wall of the uterus of the donor animal;
        providing a guide tube though which the endoscope passes;
        inserting the guide tube into the uterus through the vagina;
        holding the guide tube fixed relative to the uterus at the cervix of the uterus so as to locate an end of the guide tube at a fixed position within the uterus;
        inserting a remote end of the endoscope vaginally though the guide tube into the uterus of the donor animal to a location adjacent the embryo on the wall of the uterus of the donor animal;
        while holding the end of the guide tube fixed, operating the endoscope to move the remote end relative to the end of the guide tube to move the remote end to a position within the uterus adjacent the embryo on the wall;
        the remote end of the endoscope carrying a scoop member;
        operating the scoop member to cause the embryo to enter the scoop member from the wall of the uterus;
        the remote end of the endoscope carrying an enclosing member for covering the scoop member to enclose the embryo;
        operating the enclosing member to enclose the embryo within the scoop member;
        extracting the endoscope to remove the embryo while contained in the scoop member from the uterus of the donor animal;
        and transferring the embryo to the uterus of the recipient animal.

* * * * *